United States Patent [19]

Fukasawa et al.

[11] Patent Number: 4,792,444
[45] Date of Patent: Dec. 20, 1988

[54] COSMETIC COMPRISING FLUOROALKYL (METH)ACRYLATE COPOLYMERS

[75] Inventors: Junichi Fukasawa, Yokohama; Yutaka Yasuda, Kaizuka; Yuji Sato, Tokyo; Jun Shida, Wakayama, all of Japan

[73] Assignee: Kao Corporation, Tokyo, Japan

[21] Appl. No.: 871,649

[22] Filed: Jun. 6, 1986

[30] Foreign Application Priority Data

Jun. 14, 1985 [JP] Japan .................. 60-129613
Jul. 11, 1985 [JP] Japan .................. 60-152755

[51] Int. Cl.$^4$ .................. A61K 7/021; A61K 7/027; A61K 7/48; A61K 31/78
[52] U.S. Cl. .................. 424/63; 424/64; 424/81; 424/DIG. 5; 424/61; 514/844; 514/845; 514/772
[58] Field of Search .............. 424/63, 64, 81, DIG. 5, 424/61; 514/759, 844, 845, 743, 744, 772, 789, 846, 847; 526/245, 318, 318.4, 329.4, 936

[56] References Cited

U.S. PATENT DOCUMENTS

| Re. 29,871 | 12/1978 | Papantoniou et al. | 424/63 X |
|---|---|---|---|
| 3,378,609 | 4/1968 | Fasick et al. | 524/520 |
| 3,697,643 | 10/1972 | Sheperd et al. | 424/81 X |
| 3,960,797 | 6/1976 | Inman | 428/421 X |
| 4,423,031 | 12/1983 | Murui et al. | 424/81 X |

FOREIGN PATENT DOCUMENTS 206671 12/1986 European Pat. Off.

*Primary Examiner*—George F. Lesmes
*Assistant Examiner*—Susan S. Rucker
*Attorney, Agent, or Firm*—Flynn, Thiel, Boutell & Tanis

[57] ABSTRACT

A cosmetic agent serves to form film being durable to various effects and comprises a copolymer of a fluoroalkyl (meth)acrylate and a long chain, linear alkyl (meth)acrylate. It may further comprise a volatile oil and solid fat(s).

16 Claims, No Drawings

COSMETIC COMPRISING FLUOROALKYL (METH)ACRYLATE COPOLYMERS

This invention relates to a cosmetic. More particularly, it relates to a cosmetic that causes no irritation of the skin. The cosmetic contains copolymer(s) of long-chain alkyl (meth)acrylate(s) with (meth)acrylate(s) having a bonded fluoroalkyl group readily soluble in volatile oil for cosmetics as a film-forming component which makes said cosmetic resistant against water, oil and physical friction.

STATEMENT OF PRIOR ARTS

Conventional cosmetics may be classified into those of the aqueous, nonaqueous, emulsion and powder types. Among them, aqueous, emulsion and powder cosmetics are deteriorated by moisture such as sweat, tears, rain or snow, while emulsion, powder and nonaqueous ones are deteriorated by oil such as sebum and oily components of foods and drinks. Further each of them is deteriorated by physical friction with, for example, clothes, which makes it impossible to maintain its makeup effect.

Thus it has been attempted to add polymer(s) to a cosmetic to thereby form a film on the skin after applying the cosmetic thereon, thus improving the adhesion between pigment and solid fat contained in the cosmetic and the skin and prolonging the duration of the makeup effect.

In order to achieve this object, it has been mainly attempted to develop aqueous or emulsion type of cosmetics containing water-soluble polymers such as vinyl acetate or acrylic polymers as a film-forming component or nonaqueous type of cosmetics wherein oil-soluble polymers such as rosin, shellac or alkylcellulose are added as a film-forming component with a solvent.

However the film of a cosmetic containing water-soluble polymer(s) exhibits an unsatisfactory water resistance although it is highly resistant against oil and physical friction. Further it is difficult to prepare rigid solid products such as sticks or pencils from aqueous or emulsion type of cosmetics. On the other hand, a cosmetic containing oil-soluble polymer(s) may be blended with solid fat to thereby form a solid product such as a stick or a pencil. The solid product thus produced forms a film which exhibits an excellent water resistance and a poor oil resistance. Conventional oil-soluble polymers such as rosin, shellac or alkylcellulose can not be dissolved in volatile oil for cosmetics such as low-boiling point hydrocarbons or dimethylpolysiloxane at room temperature and, therefore, cosmetics containing the same can not be homogeneously spread on the skin or mucosa. Thus these cosmetics give an unsatisfactory touch in application and poor adhesion to the skin or mucosa and exhibit a poor frictional resistance. In addition, many natural resins including rosin and shellac would show a sensitizing activity, which brings about a problem from the viewpoint of safety. Thus conventional cosmetics containing polymer(s) are far from satisfactory from various viewpoints including the duration of the makeup effect, touch, and obtained makeup condition.

Therefore it has been required to develop a cosmetic containing highly safe polymer(s) which forms a film resistant against physical friction as well as water and oil and can be homogeneously dissolved in a solvent used for cosmetics while undergoing no decrease in the touch. It is also expected that such an cosmetic can be formulated into a solid product such as a stick or a pencil.

SUMMARY OF THE INVENTION

The invention provides a cosmetic containing as a film-forming agent a copolymer(s) of a long chain alkyl (meth)acrylate(s) and a fluoroalkyl (meth)acrylate(s). It may further comprises a volatile oil.

The invention moreover provides a cosmetic composition comprising an oil-soluble polymer, a volatile oil having a boiling point of not higher than 280° C. and solid fat(s) having a penetration of not higher than 40.

The copolymer to use in the invention is highly safe and readily soluble in a solvent mixture of low-boiling point hydrocarbons containing a large amount of highly safe volatile oil for cosmetics, such as a cyclic dimethylpolysiloxane, exhibits an excellent water resistance as well as an excellent oil resistance because of the presence of fluorine moiety in the copolymer(s) when applied to the skin, can be homogeneously spread on the skin because of its high solubility in solvents and forms a film showing satisfactory adhesion and a high frictional resistance.

We have further found that the abovementioned polymer(s) is oil-soluble and readily soluble in a solvent so that it may be formulated into solid products such as oily sticks or pencils having an extremely preferable touch and that the film-forming property of the polymer(s) and the effect of maintaining the makeup condition of the obtained film are both satisfactory, thus completing the present invention.

Accordingly, the present invention provides a cosmetic characterized by containing one or more copolymers of long-chain alkyl (meth)acrylate(s) with (meth)acrylate(s) having a bonded fluoroalkyl group as a film-forming component.

Preferable examples of the long-chain alkyl (meth)acrylate used in the present invention are esters of straight-chain or branched alkyl alcohols having eight or more carbon atoms, e.g. long-chain alcohols such as octyl, decyl, lauryl, cetyl, stearyl or behenyl alcohol with (meth)acrylic acid. Esters of long-chain alcohols having 18 or more carbon atoms are particularly preferable.

Examples of the (meth)acrylate having a bonded fluoroalkyl group are known compounds having a bonded polyfluoroalkyl or perfluoroalkyl group, such as $CH_2=CHCOOC_2H_4C_6F_{13}$, $CH_2=CHCOOC_2H_4C_8F_{17}$, $CH_2=CHCOOC_2H_4C_{10}F_{21}$, $CH_2=CHCOOC_2H_4C_{12}F_{25}$, $CH_2=C(CH_3)COOC_2H_4C_6F_{13}$, $CH_2=C(CH_3)COOC_2H_4C_8F_{17}$, $CH_2=C(CH_3)COOC_2H_4C_{10}F_{21}$, $CH_2=C(CH_3)COOC_2H_4C_{12}F_{25}$, $CH_2=CHCOOC_2H_4-(CF_2)_6-H$, $CH_2=CHCOOC_2H_4-(CF_2)_8-H$, $CH_2=C(CH_3)COOC_2H_4-(CF_2)_6-H$ and $CH_2=C(CH_3)COOC_2H_4-(CF_2)_8-H$.

In the present invention, one or more compounds obtained by copolymerizing these long-chain alkyl (meth)acrylate(s) with (meth)acrylate(s) having a bonded fluoroalkyl group may be employed.

The long-chain alkyl (meth)acrylate and (meth)acrylate having a bonded fluoroalkyl group may be copolymerized preferably in a ratio by weight of 10:1 to 1:5, still preferably 7:1 to 1:1, considering the relationship between the solubility and stickiness.

The copolymer may contain a third monomer unit.

The molecular weight of the copolymer may be preferably 1000 to 2,000,000, still preferably 10,000 to 500,000, considering the relationship between the frictional resistance and stickiness of the same.

In addition to the copolymer(s) of long-chain alkyl (meth)acrylate(s) and (meth)acrylate(s) having a bonded fluoroalkyl group, which are the essential components, the cosmetic of the present invention may further contain conventional components such as various volatile and nonvolatile oils, surfactants, wetting agents, preservatives, antioxidants, perfumes and powder constitutents if required.

The volatile oil preferably includes straight or branched hydrocarbons and cyclic dimethylpolysiloxanes, each having a boiling point of not higher than 260° C. Examples of the nonvolatile oils are straight-chain or branched hydrocarbons optionally unsaturated, synthetic ester oils derived from higher alcohols and fatty acids, higher alcohols, higher fatty acids and waxes. Examples of the surfactants are polyoxyethylene alkyl ethers, polyoxyethylene fatty acid esters, polyoxyethylene sorbitan fatty acid esters, sorbitan fatty acid esters, glycerol fatty acid esters, polyoxyethylene hardened castor oil and polyoxyethylene sorbitol fatty acid esters. Examples of the wetting agents are sorbitol, glycerol, propylene glycol, 1,3-butylene glycol, maltitol, lactic acid, sodium lactate and polyethylene glycol. Examples of the preservatives are alkyl p-hydroxybenzoates, sodium benzoates, potassium sorbate and phenoxyethanol. Examples of the antioxidants are tocopherol, sesamol, sesamolin and lecithin. Examples of the powder constituents are titanium oxide, zinc oxide, ultramarine blue, chromium oxide, iron oxide, talc, sericite, mica, kaolin, micaceous titanium and organic pigments.

The cosmetic of the present invention may furthermore contain conventional film-forming component(s) such as various resins including acrylate and vinyl acetate resins in addition to the copolymer(s) of the invention depending on the form of the products.

The copolymer(s) of long-chain alkyl (meth)acrylate(s) with (meth)acrylate(s) having a bonded fluoroalkyl group are contained in the cosmetic of the present invention preferably in an amount of 0.1 to 70% by weight, more preferably 0.5 to 40% by weight, of the total cosmetic. A content of the same lower than 0.1% by weight might result in a poor film-forming effect, while a content of the same exceeding 70% by weight might sometimes result in insufficient dispersion caused by an unbalanced composition.

When the composition contains a volatile oil, it contains 0.1 to 50 wt. %, preferably 1 to 30 wt. %, based on the oil, of the copolymer.

The cosmetic of the present invention may be prepared by, for example, mixing the essential components, i.e. copolymer(s) of long-chain alkyl (meth)acrylate(s) and (meth)acrylate(s) having a bonded fluoroalkyl group, and other components, if any, by heating with the use of, e.g., a homomixer, a homodisperser or a three-roll mixer and formulating the mixture into a desired form if required. The cosmetic of the present invention may be appropriately used as a skin cosmetic and formulated into various makeup products such as foundation, lipstick, eyeliner, mascara, pencil or rouge. These skin cosmetics may be prepared by mixing the film-forming components comprising the abovementioned copolymer(s) with volatile and nonvolatile oils including solid fats as well as other desired components by heating with the use of, for example, a homomixer, a homodisperser or a three-roll mixer and formulating the mixture into desired forms. Thus oily solid cosmetics such as sticks or pencils having excellent proprieties can be obtained.

Then the invention will be explained in reference to the second embodiment thereof. It provides an oily solid cosmetic characterized by essentially containing oil-soluble polymer(s), volatile oil(s) having a boiling point of not higher than 280° C. and solid fat having a penetration (JIS K-2530'25° C., 100 g, 5 sec) of not higher than 40.

The relationship among the oil soluble polymer(s) the volatile oil(s) and the solid fat(s) each used in the present invention is as follows. That is, the oil-soluble polymer(s) are soluble or dispersible in the volatile oil(s) but incompatible with the solid fat(s) and the solid fat(s) is insoluble in the volatile oil(s) at a temperature not higher than 40° C.

Examples of the volatile oil(s) used in the present invention are those having a boiling point not higher than 280° C., such as straight-chain dimethylpolysiloxane of a viscosity of 0.5 to 10 cSt (25° C.), cyclic dimethylpolysiloxane having a three- to six-membered ring and straight-chain or branched hydrocarbons having three to 16 carbon atoms and optionally unsaturated. One of these oils may be employed. Alternately a mixture thereof may be used.

Examples of the solid fat(s) having a penetration (JIS K-2530; 25° C., 100 g, 5 sec) not higher than 40 used in the present invention are those conventionally used for cosmetics, such as hydrocarbons having a melting point not lower than 40° C., waxes including synthetic esters derived from alcohols and fatty acids, natural waxes, higher alcohols and higher fatty acids. One of these materials may be used. Alternately a mixture thereof may be employed. It is particularly preferable to use those having a penetration (JIS K-2530; 25° C., 100 g, 5 sec) of 0.5 to 20.

The oil-soluble polymers used in the present invention are those soluble or dispersible in the volatile oils and incompatible with the solid fats. Preferable examples are as follows.

First, polymers or copolymers of vinyl monomers having a side chain comprising a long-chain alkyl group having eight or more carbon atoms, such as (meth)acrylates, maleates and fumarates of long-chain alkyl alcohols, vinyl ethers, vinyl esters of higher fatty acids or α-olefins may be preferably used. Long-chain alkyl groups having eight to 22 carbon atoms are particularly preferable. More particularly, polystearyl acrylate, polybehenyl acrylate, polystearyl methacrylate, polybehenyl methacrylate, polystearyl vinyl ether, polyvinyl stearate, $C_{12}$-α-olefin/distearyl maleate copolymer and $C_{12}$-α-olefin/distearyl fumarate copolymer may be cited. Those having a molecular weight of 5,000 to 2,000,000 are particularly preferable.

Secondly, rubber-like polymers such as polyisoprene, ethylene/propylene rubber, polybutadiene and ethylene/vinyl acetate copolymer may be cited.

In addition, copolymers of alkyl (meth)acrylates having an alkyl group having eight or more carbon atoms with (meth)acrylates having a bonded fluoroalkyl group may be employed. Examples of the alkyl (meth)acrylates having an alkyl group having eight or more carbon atoms include esters of octyl, decyl, lauryl, cetyl, stearyl or behenyl alcohol with (meth)acrylic acid. Any copolymer may be employed so long as it can be copolymerized. It is particularly preferable to use (meth)acrylate comonomers having a bonded fluoroalkyl group. Examples of the (meth)acrylates having a bonded fluoroalkyl group include well-known compounds having a polyfluoroalkyl or perfluoroalkyl group, such as $CH_2=CHCOOC_2H_4C_6F_{13}$, $CH_2=CHCOOC_2H_4C_8F_{17}$, $CH_2=CHCOOC_2H_4C_{10}F_{21}$, $CH_2=CHCOOC_2H_4C_{12}F_{25}$, $CH_2=C(CH_3)COOC_2H_4C_6F_{13}$, $CH_2C(CH_3)COOC_2H_4C_8F_{17}$, $CH_2=C(CH_3)COOC_2H_4C_{10}F_{21}$, $CH_2=(CH_3)COOC_2H_4C_{12}F_{25}$, $CH_2=CHCOOC_2H_4-(CF_2)_6-H$, $CH_2=CHCOOC_2H_4-(CF_2)_8-H$, $CH_2=C(CH_3)COOC_2H_4-(CF_2)_6-H$ and $CH_2=C(CH_3)COOC_2H_4-(CF_2)_8-H$.

These long-chain alkyl (meth)acrylates may be copolymerized with the (meth)acrylates having a bonded fluoroalkyl group in a ratio by weight of 10:1 to 1:5 considering the solubility, dispersability and stickiness thereof.

One or more oil-soluble polymers as mentioned above may be employed in the present invention.

The oily solid cosmetic of the present invention may further contain various components conventionally used in the art, such as nonvolatile oils, surfactants, wetting agents, preservatives, antioxidants, perfumes or powder constituents, in addition to the essential components as described above.

Examples of the nonvolatile oil are straightchain or branched hydrocarbons optionally unsaturated, synthetic ester oils derived from higher alcohols and fatty acids, and lecithin.

Examples of the surfactants are polyoxyethylene alkyl ethers, polyoxyethylene fatty acid esters, polyoxyethylene sorbitan fatty acid esters, sorbitan fatty acid esters, glycerol fatty acids esters, polyoxyethylene hardened castor oil and polyoxyethylene sorbitol fatty acid esters. Examples of the wetting agents are sorbitol, glycerol, propylene glycol, 1,3-butylene glycol, maltitol, lactic acid, sodium lactate and polyethylene glycol. Examples of the preservatives are alkyl p-hydroxybenzoates, sodium benzoate, potassium sorbate and phenoxyethanol. Examples of the antioxidants are tocopherol, sesamol and sesamolin. Examples of the powder constitutents are titanium oxide, zinc oxide, ultramarine blue, chromium oxide, iron oxide, talc, sericite, mica, kaolin, micaceous titanium and organic pigments.

The volatile oil(s) may be contained in the oily solid cosmetic of the present invention preferably in an amount of 5 to 80% by weight, still preferably 20 to 60% by weight. It is impossible to formulate a solid material when the content of the same exceeds 80% by weight. On the other hand, a content of the same lower than 5% by weight might give no effect.

The solid fat(s) may be contained in the oily solid cosmetic of the present invention preferably in an amount of 5 to 60% by weight, still preferably 15 to 45% by weight. A content of the same exceeding 60% by weight might result in an insufficient spreadability or poor adhesion. On the other hand, it is impossible to form sticks or pencils when the content is lower than 5% by weight.

The weight ratio of the solid fat(s) to the volatile oil(s) is preferably 0.1 to 2, still preferably 0.2 to 1.

The oil-soluble polymer(s) may be preferably contained in the cosmetic of the present invention in an amount of 0.1 to 50% by weight, still preferably 1 to 30% by weight, based on the volatile oil(s). A content of the same lower than 0.1% by weight might result in a poor frictional resistance while that exceeding 50% by weight might result in excessive stickiness or poor homogenity.

The cosmetic of the present invention may be formulated by, for example, heating and mixing the essential components, i.e. the oil-soluble polymer(s), volatile oil(s) and solid fat(s) with the use of, e.g., a homomixer, a homodisperser or a three-roll mixer followed by molding of the mixture into a desired form. The cosmetic of the present invention may be formulated into makeup products such as foundation, lipstick, eyeliner, eye shadow, eyebrow pencil and rouge.

The flexural strength of the oily solid cosmetic thus obtained is not lower than 40 g in cylindrical form of 12 mm in diameter at 25° C. and preferably within a range of 150 g and 800 g considering the shape retention and the touch.

It is below disclosed that the copolymer to use here has been produced.

REFERENTIAL EXAMPLE 1

26.7 g of perfluoroalkyl methacrylate

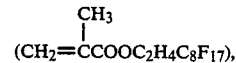

80.0 g of stearyl methacrylate and 30 g of toluene were introduced into a fournecked flask and dissolved and mixed therein followed by stirring at 50° C. for 0.5 hour under a nitrogen gas stream. Then 1.1 g of 2,2'-azobis-2,4-dimethylvaleronitrile was added thereto and the mixture was polymerized at 65° C. for five hours under a nitrogen gas stream and then at 80° C. for additional one hour to thereby give a white viscous solution. After the polymerization, the obtained solution was diluted with toluene and poured into ethanol to thereby precipitate a copolymer product, which was then filtered and dried in vacuo. Thus 102.4 g of a copolymer of perfluoroalkyl methacrylate with stearyl methacrylate was obtained.

The monomer composition of the obtained copolymer was almost the same as that of the feed (the content of the perfluoroalkyl methacrylate was 25.1% by weight).

REFERENTIAL EXAMPLE 2

The procedure of Referential Example 1 was repeated except that 50 g of perfluoroalkyl methacrylate

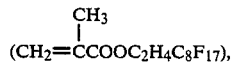

50 g of stearyl methacrylate, 50 g of toluene and 1.0 g of 2,2'-azobis-2,4-dimethylvaleronitrile were employed to thereby give 96.0 g of a copolymer of perfluoroalkyl methacrylate with stearyl methacrylate.

The content of the perfluoroalkyl methacrylate in the polymer was 49.6% by weight and almost the same as that of the feed.

REFERENTIAL EXAMPLE 3

The procedure of Referential Example 1 was repeated except that 26.7 g of polyfluoroalkyl methacrylate

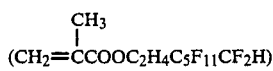

was employed to thereby give 101.4 g of a copolymer of polyfluoroalkyl methacrylate with stearyl methacrylate.

The content of the polyfluoroalkyl methacrylate in the copolymer was 24.8% by weight and almost the same as that of the feed.

REFERENTIAL EXAMPLE 4

The procedure of Referential Example 1 was repeated except that 50 g of polyfluoroalkyl methacrylate

50 g of stearyl methacrylate, 50 g of toluene and 1.0 g of 2,2'-azobis-2,4-dimethylvaleronitrile were employed to thereby give 97.0 g of a copolymer of polyfluoroalkyl methacrylate with stearyl methacrylate.

The content of the polyfluoroalkyl methacrylate in the copolymer was 50.4% by weight and almost the same as that of the feed.

REFERENTIAL EXAMPLE 5

The procedure of Referential Example 1 was repeated except that the stearyl methacrylate was replaced by behenyl methacrylate to thereby give 103.5 g of a copolymer of perfluoroalkyl methacrylate with behenyl methacrylate.

The monomer composition of the copolymer was almost the same as that of the feed (the content of the perfluoroalkyl methacrylate was 24.9% by weight based on F%).

EXAMPLE 1

The solubility of rosin ester (mfd. by Arakawa Chemicals, Co., Ltd.), which was a conventional oil-soluble film-forming agent, in a volatile oil was compared with that of each copolymer of a longchain alkyl (meth)acrylate with a (meth)acrylate having a bonded fluoroalkyl group prepared in Referential Examples 1 to 5 according to the present invention in the following manner. Table 1 shows the result.

Solubility 0.2 g of the rosin ester or the copolymer of the present invention and 1 g of a mixture of a low-boiling point hydrocarbon (IP Solvent 1620; mfd. by Idemitsu Oil Co., Ltd.) and a cyclic dimethylpolysiloxane (SH244; mfd. by Toray Silicone Co., Ltd.) were introduced in a screwed bottle followed by sealing. The mixture was stirred at 90° C. for 30 min and allowed to stand for two days. Then the dissolution state in the bottle was observed with the naked eye.

Criterion o: clear dissolution,
Δ: white dispersion,
x: separation (crystallization).

TABLE 1

| | Weight ratio of IP1620 to SH244 in solvent mixture | | | | | | | | | | |
|---|---|---|---|---|---|---|---|---|---|---|---|
| | 100/0 | 95/5 | 90/10 | 85/15 | 80/20 | 75/25 | 70/30 | 65/35 | 60/40 | 55/45 | 50/50 |
| Rosin ester | x | x | x | x | x | x | x | x | x | x | x |
| Copolymer of invention | | | | | | | | | | | |
| Ref. Ex. 1 | o | o | o | o | o | o | o | o | o | o | o |
| Ref. Ex. 2 | o | o | o | o | o | o | o | o | o | o | o |
| Ref. Ex. 3 | o | o | o | o | o | o | o | o | o | o | o |
| Ref. Ex. 4 | o | o | o | o | o | o | o | o | o | o | o |
| Ref. Ex. 5 | Δ | Δ | Δ | Δ | Δ | Δ | Δ | Δ | Δ | Δ | Δ |

| | Weight ratio of IP1620 to SH244 in solvent mixture | | | | | | | | | |
|---|---|---|---|---|---|---|---|---|---|---|
| | 45/55 | 40/60 | 35/65 | 30/70 | 25/75 | 20/80 | 15/85 | 10/90 | 5/95 | 0/100 |
| Rosin ester | x | x | x | x | x | x | x | x | x | x |
| Copolymer of invention | | | | | | | | | | |
| Ref. Ex. 1 | o | o | o | o | o | o | o | Δ | Δ | x |
| Ref. Ex. 2 | o | o | o | o | o | o | o | o | Δ | x |
| Ref. Ex. 3 | o | o | o | o | o | o | o | Δ | Δ | x |
| Ref. Ex. 4 | o | o | o | o | o | o | o | o | Δ | x |
| Ref. Ex. 5 | Δ | Δ | Δ | Δ | Δ | Δ | Δ | Δ | Δ | x |

Table 1 obviously suggests that each copolymer of the present invention has an extremely high solubility and can be dispersed or dissolved in cyclic dimethylpolysiloxane having a high safety by simply adding a small amount of the low-boiling hydrocarbon.

EXAMPLE 2

A solution of rosin ester or each copolymer prepared in Referential Examples 1 to 5 in a solvent mixture of IP1620 and SH244 of a weight ratio of 10/90 as used in Example 1 was mixed again by stirring at 90° C. for 30 min. Immediately thereafter, 1 cc of the solution was dropped on a glass plate and allowed to stand at room temperature for two days. Then properties of the films thus formed on the plates were compared with each other. Table 2 shows the result. Criterion:

o: good,
Δ: somewhat good,
x: poor.

TABLE 2

| | Appearance | Continuity | Water resistance | Oil resistance |
|---|---|---|---|---|
| Rosin ester | white and crystallized | x | o | x |
| Copolymer of invention | | | | |
| Ref. Ex. 1 | transparent | o | o | o |
| Ref. Ex. 2 | " | o | o | o |
| Ref. Ex. 3 | " | o | o | o |

TABLE 2-continued

|  | Appearance | Continuity | Water resistance | Oil resistance |
|---|---|---|---|---|
| Ref. Ex. 4 | " | o | o | o |
| Ref. Ex. 5 | translucent | Δ | o | o |

EXAMPLE 3

Lipsticks of the following composition were produced with the use of the rosin ester and the copolymers of the present invention as a film-forming agent in the following manner. The effects of use of the obtained products were compared with each other. Table 3 shows the result.

| Composition | parts by weight |
|---|---|
| film-forming agent | 10 |
| IP Solvent 1620 | 7 |
| SH244 | 49 |
| candelilla wax | 7 |
| ceresin | 3 |
| pearlescent pigment | 12 |
| titanium oxide | 1 |
| organic pigment | 1 |
|  | 100 |

Method for production

Four parts by weight of IP Solvent, one part by weight of ceresin and one part by weight of the organic pigment were mixed with a roll mill to give a pigment paste. Separately the residual amount of IP Solvent, SH244, the film-forming agent, the residual amount of the ceresin and candelilla wax were mixed by heating at 90° C. and the abovementioned pigment paste and the powder constituent were dispersed therein followed by molding in a container.

Method for test

Spreadability—Each lipstick was applied on the skin and subjected to organoleptic evaluation.

Homogeneity—do.

Frictional resistance—Each lipstick was applied on the skin, allowed to stand at room temperature for a sufficient period and subjected to repeated friction under a given pressure with a sponge puff. The color migration thus induced was observed with the naked eye.

Water resistance—Each lipstick was applied on the skin and allowed to stand at room temperature for a sufficient period. Then water was added dropwise thereto in an amount sufficient to moisten the whole film. After 10 min, the condition was observed with the naked eye.

Oil resistance—Each lipstick was applied on the skin and allowed to stand at room temperature for a sufficient period. Then liquid paraffin was added dropwise thereto in an amount sufficient to moisten the whole film. After ten min, the condition was observed with the naked eye.

Stickiness—Each lipstick was applied on the skin and allowed to stand at room temperature for a sufficient period. Then the stickiness thereof was evaluated by pressing with fingers.

Criterion

⊚ : good,
o: somewhat good,
Δ: somewhat poor,
x: poor.

TABLE 3

|  | on application | | Film formed after application | | | |
|---|---|---|---|---|---|---|
|  | Spreadability | Homogenity | Frictional resistance | Water resistance | Oil resistance | Stickiness |
| Lipstick of rosin ester | x | x | Δ | ⊚ | x | x |
| Lipstick of copolymer of Ref. Ex. 1 | ⊚ | ⊚ | ⊚ | ⊚ | ⊚ | o |
| Lipstick of copolymer of Ref. Ex. 2 | ⊚ | ⊚ | o | ⊚ | ⊚ | ⊚ |
| Lipstick of copolymer of Ref. Ex. 3 | ⊚ | ⊚ | ⊚ | ⊚ | ⊚ | o |
| Lipstick of copolymer of Ref. Ex. 4 | ⊚ | ⊚ | ⊚ | ⊚ | ⊚ | ⊚ |
| Lipstick of copolymer of Ref. Ex. 5 | ⊚ | ⊚ | ⊚ | ⊚ | ⊚ | ⊚ |

The above result suggests that each cosmetic of the present invention can be homogeneously spread on application and the film formed after the application was highly resistant against friction, water and oil, and showed a low stickiness. The stickiness tended to decrease with an increase in the chain-length of the alkyl (meth)acrylate or in the content of the fluorinated (meth)acrylate.

EXAMPLE 4

An eyeliner of the following composition was produced.

| Composition | parts by weight |
|---|---|
| copolymer of Ref. Ex. 1 | 10 |
| IP Solvent 1620 | 8 |
| SH244 | 52 |
| candelilla wax | 5 |
| ceresin | 3 |
| microcrystalline wax | 1.2 |
| black iron oxide | 20 |
| polyoxyethylene sorbitan monolaurate | 0.2 |
| glycerol monostearate | 0.4 |
| perfume | 0.2 |
|  | 100 |

The obtained eyeliner was extremely homogeneously spread and showed an excellent adhesion to the skin as well as high resistance aainst water and oil.

EXAMPLE 5

A stick-type foundation of the following composition was produced.

| Composition | parts by weight |
|---|---|
| copolymer of Ref. Ex. 4 | 10 |
| SH244 | 4 |
| IP Solvent 1620 | 39 |
| candelilla wax | 10 |
| solid paraffin | 6 |
| cerisite | 18 |
| yellow iron oxide | 4 |
| red iron oxide | 2 |
| black iron oxide | 2 |
| titanium oxide | 4.5 |
| perfume | 0.5 |

| Composition | parts by weight |
| --- | --- |
| | 100 |

The obtained foundation was extremely homogeneously spread and showed an excellent adhesion to the skin as well as high resistance against water and oil with little stickiness.

EXAMPLE 6

A stick-type eye shadow of the following

| Composition | parts by weight |
| --- | --- |
| copolymer of Ref. Ex. 5 | 10 |
| IP Solvent 1620 | 4 |
| SH244 | 39 |
| candelilla wax | 8 |
| ceresin | 5 |
| pearlescent pigment | 20 |
| mica | 12 |
| titanium oxide | 1.8 |
| perfume | 0.2 |
| | 100 |

The obtained eye shadow was homogeneously spread and showed an excellent adhesion to the skin as well as high resistance against water and oil with little stickiness.

EXAMPLE 7

An oily, solvent type mascara of the following composition was produced.

| Composition | parts by weight |
| --- | --- |
| copolymer of Ref. Ex. 2 | 15 |
| solid paraffin | 15 |
| IP Solvent | 55 |
| SH244 | 5 |
| pigment | 10 |
| perfume | a trace amount |

Method for production

Some portion of IP Solvent, SH244 and some portions of the copolymer and solid paraffin were mixed together and dissolved by heating. Separately the residual IP Solvent was mixed with the residual solid paraffin and the pigment paste was added thereto. The mixture was mixed with a roll mill and dispersed in the copolymer liquid part followed by cooling.

Evaluation

The obtained mascara applied on eyelashes was highly resistant against water, i.e. not washed away by tears. It was further resistant against friction such as winks.

EXAMPLE 8

A stick-type eyebrow pencil of the following composition was produced.

| Composition | parts by weight |
| --- | --- |
| copolymer of Ref. Ex. 5 | 10 |
| IP Solvent | 7 |
| SH 244 | 35 |
| ceresin | 1 |
| solid paraffin | 36 |
| pigment | 11 |

Method for production

All materials other than the pigmnt were molten and the pigment was added and thoroughly dispersed therein. The dispersion was mixed with a heated roll mill several times, cooled to room temperature and extruded with an extruder having a nozzle of an internal diameter of 3 mm.

Evaluation

The obtained eyebrow pencil was resistant against water and friction and hardly deteriorated.

EXAMPLE 9

A fingernail polish of the following composition was produced.

| Composition | parts by weight |
| --- | --- |
| copolymer of Ref. Ex. 2 | 12 |
| nitrocellulose | 15 |
| camphor | 6 |
| butyl acetate | 25 |
| ethanol | 7 |
| toluene | 30 |
| colorant | an appropriate amount |

The obtained fingernail polish was appropriate for application and showed an excellent adhesion to the nail.

The invention will be further illustrated with working examples in reference to the embodiment in which the cosmetic composition comprises an oil-soluble polymer, a volatile oil having a boiling point of not higher than 280° C. and solid fat(s) having a penetration of not higher than 40.

EXAMPLE 10

Lipsticks of the composition A as shown in Table 4 were produced in the following manner wherein polystearyl methacrylate, polybehenyl methacrylate, polystearyl vinyl ether, polyisoprene, ethylene/propylene rubber or ethylene/vinyl acetate copolymer were employed as the oil-soluble polymer and low-boiling point isoparaffin (IP Solvent 1620; mfd. by Idemitsu Oil Co., Ltd.) and cyclic dimethylpolysiloxane (SH-244; mfd. by Toray Silicone Co., Ltd.) were employed as the volatile oils. The effect of preventing color migration of each lipstick was evaluated. In addition, a product containing ceresin and micaceous titanium in excessive amounts instead of the oil-soluble polymer (Composition B in Table 4) and that containing liquid paraffin instead of the oil-soluble polymer and the volatile oils (Composition C in Table 4) were produced for comparison.

Production of lipstick

Four parts by weight of IP Solvent 1620, one part by weight of ceresin and one part by weight of red colorant No. 202 are mixed together in a three-roll mixer to give a paste. Then the whole composition was mixed in a sealed container by heating to 90° C. for 30 min and poured into given molds followed by cooling at −5° C. for 20 min therein.

Evaluation of color migration

The color migration was evaluated by applying a lipstick on 1 cm² of the human skin until the skin color could not be observed. After allowing to stand for one min, a sheet of tissue was pressed against the applied area under a given pressure, or a sheet of tissue applied on the skin was displaced laterally under a given pressure while it was pressed thereagainst. The density of the color of the lipstick migrated to the tissue by each of the above treatments was evaluated with the naked eye according to the following criterion.

Criterion

The color of the tissue was given point 0, while the density of the color migrated to the tissue when pressing the lipstick of Composition C with the tissue and laterally displacing the tissue while it was pressed thereagainst was given point 5.

Each lipstick was applied on 1 cm² of the human skin until the color of the skin could not be observed and allowed to stand for one min. Then a drop of liquid paraffin was placed thereon with a capillary and a sheet of tissue was pressed thereagainst. The color of the lipstick thus migrated to the tissue was evaluated according to the above criterion.

Table 4 shows the compositions of the lipsticks while Table 5 shows the evaluation of the color migration to the tissue.

TABLE 4

| Composition | (parts by weight) | | |
| --- | --- | --- | --- |
| | A | B | C |
| oil-soluble polymer | 10 | 0 | 0 |
| IP Solvent 1620 | 16 | 16 | 0 |
| SH244 | 40 | 40 | 0 |
| candelilla wax | 7 | 7 | 7 |
| ceresin | 13 | 18 | 18 |
| micaceous titanium | 12 | 17 | 17 |
| titanium oxide | 0.5 | 0.5 | 0.5 |
| red colorant No. 202 | 1.5 | 1.5 | 1.5 |
| liquid paraffin | 0 | 0 | 56 |

TABLE 5

| Composition | Oil-soluble polymer | Pressed | Displaced | Oil drop placed followed by pressing |
| --- | --- | --- | --- | --- |
| A | polystearyl methacylate (synthetic, MW: 40,000) | 0 | 1 | 1 |
| | polybehenyl methacylate (synthetic, MW: 73,000) | 0 | 1 | 1 |
| | polystearyl vinyl ether (mfd. by BASF, Wax V) | 1 | 2 | 2 |
| | polyisoprene (mfd. by Kuraray Co., Ltd.) | 2 | 3 | 3 |
| | ethylene/propylene rubber (mfd. by Japan Synthetic Rubber Co., Ltd., EPOIP) | 2 | 3 | 3 |
| | ethylene/vinyl acetate copolymer (mfd. by Mitsubishi Petrochemical Co., Ltd., Mizette 177, containing 20.9% by weight of vinyl acetate) | 2 | 3 | 2 |
| B | | 1 | 4 | 5 |
| C | | 5 | 5 | 5 |

The result of this evaluation, evidently shows that the cosmetic of the present invention is highly resistant against oil and exhibits a high effect of preventing color migration.

EXAMPLE 11

The procedure of Example 10 was repeated except using a cylindrical mold of 12 mm in diameter to thereby produce a stick-type of oily foundation of the following composition and the effect of preventing color migration of the same was evaluated. Further the flexural strength thereof was determined at 25° C. with a rheometer (mfd. by Fudo Kogyo Co., Ltd.).

| Composition | parts by weight |
| --- | --- |
| polystearyl methacrylate | 10 |
| IP Solvent 1620 | 16 |
| SH244 | 30 |
| candelilla wax | 7 |
| ceresin | 18 |
| cerisite | 10 |
| kaolin | 5 |
| red iron oxide | 3 |
| yellow iron oxide | 0.5 |
| perfume | 0.5 |
| Total | 100 |

The obtained foundation showed an excellent spreadability while giving no dryness after application and little color migration. The flexural strength thereof was 80 g.

EXAMPLE 12

A stick-type of oily eyeliner of the following composition was produced and the effect of preventing color migration and the flexural strength (25° C.) of the same were evaluated.

| Composition | parts by weight |
| --- | --- |
| ethylene/propylene rubber | 10 |
| IP Solvent 1620 | 15 |
| SH244 | 25 |
| candelilla wax | 7 |
| microcrystalline wax | 18 |
| solid paraffin | 10 |
| black iron oxide | 14.5 |
| perfume | 0.5 |
| Total | 100 |

The obtained eyeliner showed and excellent spreadability an was highly resistant against sweat and sebum while causing little color migration. The flexural strength of the same was 70 g.

EXAMPLE 13

An oily eyebrow pencil of the following composition was produced and the effect of preventing color migration and the flexural strength (25° C.) of the same were evaluated.

| Composition | parts by weight |
| --- | --- |
| stearyl methacylate/perfluoroalkyl methacrylate copolymer *1 | 10 |
| IP Solvent 1620 | 15 |
| SH244 | 20 |
| candelilla wax | 12 |
| microcrystalline wax | 18 |
| solid paraffin | 10 |
| black iron oxide | 10.5 |
| perfume | 0.5 |
| Total | 100 |

*1 A copolymer of stearyl methacylate with perfluoroalkyl methacrylate in a weight ratio of 3/1. $CH_2=C(CH_3)-COOC_2H_4C_8F_{17}$ was used as the perfluoroalkyl methacrylate.

The obtained eyebrow pencil showed an excellent spreadability and was highly resistant against sebum and sweat while causing little color migration. The flexural strength of the same was 75 g.

The embodiments of the invention in which an exclusive property of privilege is claimed are defined as follows:

1. A cosmetic composition comprising
   (a) from 5 to 80 percent by weight of a cosmetically acceptable volatile oil component having a boiling point of not higher than 280° C.;
   (b) from 0.1 to 50 percent by weight, based on the weight of said volatile oil component, of at least one copolymer of (i) a first monomer selected from the group consisting of fluoroalkyl acrylates and fluoroalkyl methacrylates and (ii) a second monomer selected from the group consisting of $C_8-C_{22}$ alkyl acrylates and $C_8-C_{22}$ alkyl methacrylates, the weight ratio of said second monomer to said first monomer being in the range of from 10:1 to 1:5, said copolymer being dissolved in said volatile oil, and
   (c) the balance is one or more conventional ingredients for cosmetics.

2. The cosmetic composition according to claim 1 in which said volatile oil component is a mixture of low boiling point hydrocarbon and dimethylpolysiloxane.

3. The cosmetic composition according to claim 1, in which said fluoroalkyl group is a perfluoroalkyl group or a polyfluoroalkyl group having at least 4 carbon atoms.

4. The cosmetic composition according to claim 1, containing from 20 to 60 percent by weight of said volatile oil component and the amount of said copolymer is from 1 to 30 percent by weight, based on said volatile oil component.

5. The cosmetic composition according to claim 1, in which the weight ratio of said second monomer to said first monomer is from 7:1 to 1:1.

6. The cosmetic composition according to claim 1, in which the molecular weight of said copolymer is from 1,000 to 2,000,000.

7. The cosmetic composition according to claim 1, in which said second monomer is an ester of acrylic acid or methacrylic acid with an alcohol selected from the group consisting of octyl alcohol, decyl alcohol, lauryl alcohol, cetyl alcohol, stearyl alcohol and behenyl alcohol.

8. A solid, skin makeup, cosmetic composition comprising
   (a) from 5 to 80 percent by weight of a volatile oil component having a boiling point of not higher than 280° C.;
   (b) from 0.1 to 50 percent by weight, based on the weight of said volatile oil component, of at least one copolymer of (i) a first monomer selected from the group consisting of fluoroalkyl acrylates and fluoroalkyl methacrylates and (ii) a second monomer selected from the group consisting of $C_8-C_{22}$ alkyl acrylates and $C_8-C_{22}$ alkyl methacrylates, the weight ratio of said second monomer to said first monomer being in the range of from 10:1 to 1:5, said copolymer being dissolved in said volatile oil, and
   (c) from 5 to 60 percent by weight of a solid fat having a penetration of 40 (determined by Japanese Industrial Standard K-25 30, 25° C., 100 g, 5 sec), said copolymer being soluble or dispersible in said volatile oil and being incompatible with said solid fat, said solid fat being insoluble in said volatile oil at a temperature not higher than 40° C.; and
   (d) the balance is one or more conventional ingredients for skin makeup cosmetics.

9. The cosmetic composition according to claim 8 in which said volatile oil component is a mixture of low boiling point hydrocarbon and dimethylpolysiloxane.

10. The cosmetic composition according to claim 8 in which said fluoroalkyl group is a perfluoroalkyl group or a polyfluoroalkyl group having at least 4 carbon atoms.

11. The cosmetic composition according to claim 8 containing from 20 to 60 percent by weight of said volatile oil component and from 15 to 45 percent by weight of said solid fat, the amount of said copolyumer is from 1 to 30 percent by weight, based on said volatile oil component.

12. The cosmetic composition according to claim 8 in which the weight ratio of said second monomer to said first monomer is from 7:1 to 1:1.

13. The cosmetic composition according to claim 8 in which the molecular weight of said copolymer is from 1,000 to 2,000,000.

14. The cosmetic composition according to claim 8 in which said second monomer is an ester of acrylic acid or methacrylic acid with an alcohol selected from the group consisting of octyl alcohol, decyl alcohol, lauryl alcohol, cetyl alcohol, stearyl alcohol and behenyl alcohol.

15. The cosmetic composition according to claim 8 in which said solid fat has a penetration of 0.5 to 20 and is selected from hydrocarbons having a melting point not lower than 40° C., waxes, higher alcohols and higher fatty acids.

16. The cosmetic composition according to claim 8 in which the weight ratio of said solid fat to said volatile oil is from 0.1/1 to 2/1.

* * * * *

UNITED STATES PATENT AND TRADEMARK OFFICE
CERTIFICATE OF CORRECTION

PATENT NO. : 4 792 444
DATED : December 20, 1988
INVENTOR(S) : Junichi FUKASAWA et al It is certified that error appears in the above-identified patent and that said Letters Patent is hereby corrected as shown below:

Column 15, line 32; change "280? C" to ---280°C---.
Column 16, line 41; change "copolyumer" to ---copolymer---.

Signed and Sealed this

Twenty-fifth Day of July, 1989

Attest:

DONALD J. QUIGG

Attesting Officer

Commissioner of Patents and Trademarks